United States Patent
Butler et al.

(10) Patent No.: US 6,426,214 B1
(45) Date of Patent: *Jul. 30, 2002

(54) CELL ENCAPSULATING DEVICE CONTAINING A CELL DISPLACING CORE FOR MAINTAINING CELL VIABILITY

(75) Inventors: Mark D. Butler; Stanley L. Mish, both of Flagstaff, AZ (US)

(73) Assignee: Gore Enterprise Holdings, Inc., Newark, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 09/435,510

(22) Filed: Nov. 8, 1999

Related U.S. Application Data

(63) Continuation of application No. 08/906,367, filed on Aug. 5, 1997, now Pat. No. 5,980,889, which is a continuation of application No. 08/320,417, filed on Oct. 5, 1994, now abandoned, which is a continuation of application No. 08/105,011, filed on Aug. 10, 1993, now abandoned.

(51) Int. Cl.[7] .......................... C12M 3/00; C12M 11/04; C12M 5/00; A01N 63/00; C12P 21/04

(52) U.S. Cl. ................... 435/289.1; 424/93.7; 424/423; 435/70.3; 435/71.1; 435/71.2; 435/177; 435/180; 435/182; 435/382; 435/395; 435/401; 435/402; 435/403

(58) Field of Search ............................. 424/93.7, 423; 435/289.1, 70.1, 70.3, 71.1, 71.2, 177, 180, 182, 382, 395, 401, 402, 403

(56) References Cited

U.S. PATENT DOCUMENTS

| | | | |
|---|---|---|---|
| 3,993,072 A | 11/1976 | Zaffaroni | 424/430 |
| 4,298,002 A | 11/1981 | Ronel et al. | 424/424 |
| 4,323,457 A | 4/1982 | Sen et al. | 210/645 |
| 4,353,888 A | 10/1982 | Sefton | 424/424 |
| 4,378,016 A | 3/1983 | Loeb | 424/424 |

(List continued on next page.)

FOREIGN PATENT DOCUMENTS

| | | |
|---|---|---|
| EP | 0 147 939 | 10/1985 |
| EP | 0 213 908 | 3/1987 |
| EP | 0 290 166 | 11/1988 |
| EP | 0 331 521 | 9/1989 |
| EP | 0 359 575 | 3/1990 |
| EP | 0 457 430 | 11/1991 |
| EP | 0 504 781 | 9/1992 |
| WO | WO 84/01287 | 4/1984 |
| WO | WO 90/01498 | 2/1990 |
| WO | WO 90/12604 | 11/1990 |
| WO | WO 90/15637 | 12/1990 |
| WO | WO 91/00119 | 1/1991 |
| WO | WO 91/10425 | 7/1991 |
| WO | WO 91/10470 | 7/1991 |
| WO | WO 92/07525 | 5/1992 |
| WO | 9219195 | * 11/1992 |
| WO | WO 93/08850 | 5/1993 |
| WO | WO 93/19701 | 10/1993 |
| WO | WO 93/21902 | 11/1993 |
| WO | WO 93/22427 | 11/1993 |
| WO | WO 94/07999 | 4/1994 |
| WO | WO 95/18583 | 7/1995 |

OTHER PUBLICATIONS

Calafiore, et al., "Vascular Graft of Microencapsulated Human Pancreatic Islets in Nonimmunosuppressed Diabetic Recipients: Preliminary Results", *Diab. Nutr. Metab.*, 4:45–48, Feb. 1991.

Hughes, et al., "Engineering of Glucose–stimulated Insulin Secretion and Biosynthesis in Non–islet Cells", *Proc. Natl. Acad. Sci., U.S.A.*, 89:688–692, Jan. 1992.

Lienhard, et al., "How Cells Absorb Glucose", *Scientific American*, Jan. 1992, pp 34–39.

Monaco, et al., "Transplantation of Islet Allografts and Xenografts in Totally Pancreatectomized Diabetic Dogs Using the Hybrid Artificial Pancreas", *Ann. Surg.*, 214:339–362, Sep. 1991.

Reach, "Artificial and Bioartificial Replacement of the Endocrine Pancreas", *Artificial Organs*, 16:61–70, 1992.

Schrezenmeir, et al., "The Role of Oxygen Supply in Islet Transplantation", *Transplantation Proceedings*, 24:2925–2929, Dec. 1992.

(List continued on next page.)

*Primary Examiner*—David M. Naff
(74) *Attorney, Agent, or Firm*—Morgan & Finnegan, L.L.P.; Kenneth H. Sonnenfeld

(57) ABSTRACT

Cell encapsulating devices capable of maintaining large numbers of viable cells are provided containing an inert, substantially cell-free core that displaces cells, a permeable membrane and a zone for maintaining cells. The permeable membrane surrounds the core such that the zone of cells is bounded by the core and the permeable membrane. A preferred device contains a polytetrafluoroethylene permeable membrane and a flexible polymer core having a plurality of ridges and valleys running lengthwise along the core. The cell zone may contain support means for cell attachment and the core may have an outer boundary containing a material that promotes cell adhesion. Preferably, the cell zone has a thickness such that at least about 10% of the cells, more preferably at least about 50% or 80%, in a cell layer located closest to the outer boundary of the core remain viable. The thickness is preferably less than 500 microns such as 25 to 250 microns or 50 to 100 microns. The devices are suitable for implantation into an individual in need of treatment and are capable of supplying therapeutic substances to such individuals.

1 Claim, 5 Drawing Sheets

U.S. PATENT DOCUMENTS

| | | | | |
|---|---|---|---|---|
| 4,391,909 | A | 7/1983 | Lim | 435/1.1 |
| 4,409,331 | A | 10/1983 | Lim | 435/178 |
| 4,420,589 | A | 12/1983 | Stoy | 525/93 |
| 4,495,288 | A | 1/1985 | Jarvis, Jr. et al. | 435/382 |
| 4,505,266 | A | 3/1985 | Yannas et al. | 128/898 |
| 4,631,188 | A | 12/1986 | Stoy et al. | 424/78.18 |
| 4,663,286 | A | 5/1987 | Tsang et al. | 435/178 |
| 4,673,566 | A | 6/1987 | Goosen et al. | 424/424 |
| 4,686,098 | A | 8/1987 | Kopchick et al. | 424/424 |
| 4,722,898 | A | 2/1988 | Errede et al. | 435/182 |
| 4,743,545 | A | 5/1988 | Torobin | 435/41 |
| 4,789,550 | A | 12/1988 | Hommel et al. | 424/493 |
| 4,803,168 | A | 2/1989 | Jarvis, Jr. | 424/493 |
| 4,806,355 | A | 2/1989 | Goosen et al. | 424/424 |
| 4,892,538 | A | 1/1990 | Aebischer et al. | 604/891.1 |
| 4,902,295 | A | 2/1990 | Walthall et al. | 623/11 |
| 4,911,717 | A | 3/1990 | Gaskill, III | 623/11 |
| 4,941,812 | A | 7/1990 | Samelson | 425/131.5 |
| 4,942,129 | A | 7/1990 | Goosen et al. | 435/182 |
| 4,969,705 | A | 11/1990 | Stoy et al. | 385/96 |
| 4,997,443 | A | 3/1991 | Walthall et al. | 623/11 |
| 5,002,661 | A | 3/1991 | Chick et al. | 210/192 |
| 5,011,486 | A | 4/1991 | Aebischer et al. | 606/152 |
| 5,017,490 | A | 5/1991 | Taiariol et al. | 435/401 |
| 5,030,225 | A | 7/1991 | Aebischer et al. | 606/152 |
| 5,081,035 | A | 1/1992 | Halberstadt et al. | 435/297.4 |
| 5,084,350 | A | 1/1992 | Chang et al. | 428/402.2 |
| 5,100,392 | A | 3/1992 | Orth et al. | 404/175 |
| 5,106,627 | A | 4/1992 | Aebischer et al. | 424/424 |
| 5,109,866 | A | 5/1992 | Guegan et al. | 128/771 |
| 5,116,493 | A | 5/1992 | Chick et al. | 210/192 |
| 5,116,494 | A | 5/1992 | Chick et al. | 210/192 |
| 5,116,753 | A | 5/1992 | Beattie et al. | 435/34 |
| 5,158,881 | A | 10/1992 | Aebischer et al. | 435/182 |
| 5,182,111 | A | 1/1993 | Aebischer et al. | 424/424 |
| 5,284,761 | A | 2/1994 | Aebischer et al. | 435/182 |
| 5,314,471 | A | 5/1994 | Brauker et al. | 623/11 |
| 5,344,454 | A | 9/1994 | Clarke et al. | 623/11 |
| 5,418,154 | A * | 5/1995 | Aebischer et al. | 435/182 |
| 5,453,278 | A | 9/1995 | Chan et al. | 424/422 |
| RE35,653 | E * | 11/1997 | Aebischer et al. | 604/891.1 |
| 5,980,889 | A * | 11/1999 | Butler et al. | 424/93.7 |

OTHER PUBLICATIONS

Selam, et al., "Devices for Insulin Administration", *Diabetes Care*, 13:955–979, Sep. 1990.

Dinsmoor, "Miracle Membranes", *Countdown*, 13:34–39, 1992.

Sullivan, et al., "Biohybrid Artificial Pancreas: Long–Term Implantation Studies in Diabetic, Pancreatectomized Dogs", *Science*, 252:718–721, May 1991.

Colton, et al., "Bioengineering in Development of the Hybrid Artificial Pancreas", *J. Biomech. Eng.*, 113:152–170, 1991.

Lacy, et al. "Maintenance of Normoglycemia in Diabetic Mice by Subcutaneous Xenografts of Encapsulated Islets", *Science*, 254:1782–1784, 1991.

Dionne, et al., "Effect of Hypoxia on Insulin Secretion by Isolated Rat and Canine Islets of Langerhans", *Diabetes*, 42:12–20, 1993.

Jauregui, et al., "Hybrid Artificial Liver", in *Biocompatible Polymers, Metals and Other Composites*, Szycher, M. (ed)., Lancaster, PA Technomic Pub., 1983, 907–928.

Aebischer, et al. "Transplantation of Polymer Encapsulated Neurotransmitter Secreting Cells: Effect of the Encapsulation Technique", *J. Biomech. Eng.*, 113:178–183, 1991.

Guénard, et al. "Syngeneic Schwann Cells Derived From Adult Nerves Seeded in Semipermeable Guidance Channels Enhance Peripheral Nerve Regeneration", *J. Neuroscience*, 12:3310–3320, 1992.

Ohgawara, et al. "Successful Implantation of Cultured Allo– And Xenograft Islets With The Use of A Diffusion Chamber", *Life Support Systems*, 3 Suppl 1: (645–8), 1985.

Theodorou, et al. "An Assessment of Diffusion Chambers For Use in Pancreatic Islet Cell Transplantation", *Transplantation*, 27:350–353; 1978.

Tresco, et al. "Polymer Encapsulated Neurotransmitter Secreting Cells: Potential Treatment for Parkinson's Disease", *ASA10 J.*, 38:17–23, 1992.

Guénard, et al., "Influence of Surface Texture of Polymeric Sheets on Peripheral Nerve Regeneration In a Two–Compartment Guidance System", *Biomaterials*, 12:259–263, 1991.

Jaeger, et al., "Repair of the Blood–Brain Barrier Following Implantation of Polymer Capsules" *Brain Research*, 551:163–170, 1991.

Jaeger, et al., Polymer Encapsulated Dopaminergic Cell Lines As 'Alternative Neural Grafts', *Prog. Brain Res.*, 82:41–46, 1990.

Scharp, et al. "Islet Immuno–isolation: The Use of Hybrid Artificial Organs to Prevent Islet Tissue Rejection", *World J. Surg.*, 8:221–229, 1984.

Altman, et al., "Long–Term Plasma Glucose Normalization in Experimental Diabetic Rats With Macroencapsulated Implants of Benign Human Insulinomas", *Diabetes*, 35:625–633 (1986).

Sun et al., *Diabetes*: 26:1136–1139 (1977).

Tze et al., *Nature*: 264:466–467 (1976).

* cited by examiner

CELL ENCAPSULATING DEVICE CONTAINING A CELL DISPLACING CORE FOR MAINTAINING CELL VIABILITY

This is a continuation co-pending application Ser. No. 08/906,367 filed Aug. 5, 1997 now U.S. Pat. No. 5980,889 which is a continuation of application Ser. No. 08/320,417, filed Oct. 5, 1994, now abandoned, which is a continuation of application Ser. No. 08/105,011, filed Aug. 10, 1993, now abandoned.

TECHNICAL FIELD OF THE INVENTION

This invention relates to devices useful for maintaining cells in a discrete space while permitting passage of cell nutrients and waste products in and out of the device. The devices of this invention are suitable for implanting in an individual who would benefit from exposure to products produced by the cells which diffuse out of the device. The invention also relates to purification of cell products from the in vitro growth of cells.

BACKGROUND OF THE INVENTION

Transplanted cells provide the potential for treating various diseases because of their ability to detect and respond to physiologically important substances in the host. Cell implantation therapy is particularly desirable because the cells can provide substances to replace or supplement natural substances which, due to their insufficiency or absence cause disease. The release of therapeutic substances from the transplanted cells may also be properly regulated provided the transplanted cells have the necessary receptors and ability to respond to endogenous regulators.

Patients having disease as a result of the loss or deficiency of hormones, neurotransmitters, growth factors or other physiological substances are considered to be among those who would achieve significant benefits from transplant therapy. For example, implantation of pancreatic islet cells could provide insulin as needed to a diabetic. Adrenal chromaffin cells or PC12 cells implanted in the brain may provide dopamine to treat patients with Parkinson's disease. Several other hormones, growth factors and other substances have been identified and are discussed in PCT application WO 92/19195 (which is incorporated herein by reference), as potential therapeutics which could be administered to an individual using transplanted cells.

Because cells which are implanted may be foreign to the host it is necessary to prevent the host immune system from attacking and thereby causing the death of the implanted cells. In addition, cells which secrete such therapeutic substances may have been derived from transformed cells or have been infected with viruses and may therefore present a potential threat to the host in the form of increasing the likelihood of tumor formation. At least four methods are possible to attenuate the host immune response for the purposes of protecting the transplant cell viability. One method involves immunosuppression to prevent transplant rejection. Immunosuppression may be accomplished through a variety of methods, including using immunosuppressive drugs such as cyclosporins. In another method, immunomodulation, the antigenicity of the implanted cells is altered. This could involve attaching antibody fragments to the implanted cells. The third method involves modulating the host immune system to obtain tolerance to the implanted cells. In a fourth method, the cells to be implanted are contained in a device which effectively isolates the implanted cells from the immune system. The ability of contained cells to manufacture and secrete substances of therapeutic value has led to the development of implantable devices for maintaining cells within an individual in need of treatment.

A common feature of isolation devices is a colony of living cells surrounded by a permeable membrane. The transport of nutrients, waste and other products across the membrane is driven by pressure and/or diffusion gradients. This movement of substances across the membrane is limited by the permeability of the membrane and the distance through which these substances must travel. If insufficient transport of these substances is provided for either the number or volume of cells, cell viability and function may be diminished.

Dionne, has reported that a dense metabolically active cell mass must not exceed certain maximum dimensions if the viability of the entire cell mass is to be maintained. "Effect of Hypoxia on Insulin Secretion by Isolated Rat and Canine Islets of Langerhans", *Diabetes*, Vol. 42, 12:20, (January 1993). When large spheroidal cell agglomerates receive nutrition from an external source, cells at the center of the cell mass may not receive sufficient nutrition and die.

Most encapsulation devices feature larger cell chambers than will allow diffusion of a sufficient flux of nutrients to support a viable full density cell mass. A full density cell mass is the maximum number of cells which can be maintained in a fixed volume if the entire space available for cells is occupied by the cells to achieve a minimum of cell-free space. This number is approximated by dividing the total available volume for containing cells by the volume of a single cell.

In the cylindrical devices referred to by Aebischer in WO 92/19595, the diameter is larger than the maximum diameter which would support a viable full density cell mass. Accordingly, the cells of the device described in Wo 92/19595 must be in a diluted suspension at a lesser cell density. The diluted cell suspension has lower overall nutrient requirements per unit volume and thus maintains essentially full viability with the available nutrient transported through the permeable membrane. The larger than optimum cell container allows for easier manufacture and subsequent manipulation than would be possible if this device were made small enough to support an optimum, full density cell pack. Aebischer also refers to the use of a gelling substance in the cell suspension to immobilize the cells into a uniform dispersion to prevent aggregation of cells into clumps. Such clumps could otherwise become necrotic due to localized depletion of nutrients within these clumps.

Several immunoisolating devices have been developed for implanting cells in a host. U.S. Pat. No. 5,158,881, refers to a device in which cells are stated to be encapsulated within a semipermeable, polymeric membrane by co-extruding an aqueous cell suspension of polymeric solution through a common port to form a tubular extrudate having a polymeric outer coating which encapsulates the cell suspension. In one embodiment described in the U.S. Pat. No. 5,158,881 patent, the cell suspension and polymeric solution are extruded through a common extrusion port having at least two concentric bores, such that the cell suspension is extruded through the inner bore and the polymeric solution is extruded through the outer bore. The polymeric solution is stated to coagulate to form an outer coating. In another embodiment of the 5,158,881 patent, the tubular extrudate is sealed at intervals to define separate cell compartments connected by polymeric links.

A different approach to supply nutrients to an isolation device is to route a flowing blood supply or other physiologic fluid through one or more conduits within the cell mass. This internalized source of nutrient mimics the structure of the circulatory system of almost all complex organisms, by providing nutrient to the center of a cell mass or tissue. These nutrients then diffuse radially outward. In one such internally fed device described in WO 91/02498, the transplanted cells are contained in-between two concentric tubes. One end of the inner tube is grafted to an artery while the other end is grafted to a vein. A common problem with internally fed devices is the potential for thrombosis formation or clotting of blood within the artificial conduits which occurs in relatively short periods of time. The formation of such obstructing masses cut off the flow of nutrients to internally fed devices.

In another device described by Goosen, U.S. Pat. Nos. 4,673,566, 4,689,293 and 4,806,355, the cells are contained in a semisolid matrix which is encapsulated in a biocompatible semipermeable electrically charged membrane. The membrane is stated to permit the passage of nutrients and factors while excluding viruses, antibodies and other detrimental agents present in the external environment.

W084/01287 refers to devices for encapsulating genetically programmed living organisms. One of the devices referred to comprises a nutrient material surrounded by an inner membrane wall which is surrounded by a layer of organisms surrounded by an outer membrane wall. The organisms are stated to provide therapeutic substances. These organisms receive nutrients from the inner layer. Including a nutrient layer in the center of the device makes the manufacture of such devices difficult and expensive.

For implanted devices to be therapeutic, enough cells must be present and viable within the device to manufacture and secrete therapeutically effective amounts of a therapeutic substance. If too many cells are consuming nutrients within the device, the local concentration of these solutes will drop below the minimum level required for cell viability. Cells which are located near the outer surface of the cell mass will typically receive ample nutrition, while cells located in the interior will be the first to die or otherwise become disabled. Factors which may have a negative effect on the viability of cells contained within a device are: device dimensions which position cells far from nutrients; cells with high metabolic demand; and any resistance to diffusive transport resulting from thick or impermeable membranes or unstirred fluid layers. Cell masses which become too large may inhibit diffusion of nutrients or gasses into the depths of the cell mass, resulting in the death of such cells and a correspondingly decreased substance output. This phenomenon is reported by Schrezenmeir, et al., in "The Role of Oxygen Supply in Islet Transplantation", *Transplantation Proceedings*, Vol. 24, No. 6, pp. 2925:2929, (1992), which reports a central core of necrosis in islets greater than about 150 microns diameter after culturing of the islets in an encapsulating device. Additionally, the secretion of other factors associated with lysis of dead cells may be harmful to the host or adjacent cells.

Another method for maintaining the viability of cells within an encapsulating device is to make the device sufficiently narrow to keep the cells sufficiently close to the permeable membrane in contact with the environment. Decreasing the device diameter however, results in a finer, more fragile structure which is increasingly hard to manufacture and use.

Another requirement of encapsulation devices is that the device must have sufficient mechanical strength and a geometry suitable for allowing the device to be manipulated by a surgeon during implantation. Mechanical integrity allows immunoisolating devices to be manipulated as a unit. Strength requirements will vary with the size, weight and shape of the device, but in general, the longer, heavier, or larger the device, the stronger it will have to be. As the number of cells required to provide therapeutic benefit increases, the size of the device and the amount of structural material must also increase. The additional structural material necessary to manufacture a larger device may interfere with the function of the device if it reduces cell viability or the transport of therapeutic substances. Suitable geometries for implantation might include a size and shape which can be handled aseptically using gloved hands and surgical instruments, and which will fit in the intended implant sites within the host.

Various methods have been described for filling devices with living cells. Some devices are filled after the permeable membrane is formed by flushing a cell suspension into the device, while other devices are produced by forming a membrane around the cell mass using a chemical process which causes the membrane to form without killing cells. In the former, the device is easier to load with viable cells if the dimensions of the device are large enough to allow low shear flow of the cell suspension. In the latter example, larger device dimensions also enhance manufacturability as a greater proportion of cells remain viable because they are protected from the membrane formation process by the presence of an unstirred fluid layer and are more distant from the site of membrane formation. A disadvantage of larger device dimensions occurs when cells near the surface are triggered to respond to a stimulus which may not reach cells situated more internally therefore diminishing the release of the therapeutic substance from the internally situated cells.

It is therefore necessary to develop a device of suitable geometry and strength which can provide an adequate number of viable cells and which may be inserted in an individual.

SUMMARY OF THE INVENTION

This invention provides an implantable device for providing therapeutic substances to an individual in need of treatment. The invention maximizes the proportion of cells in close proximity to a membrane in contact with the environment while maintaining a geometry which is practical for implantation in the individual. This is accomplished by providing a device comprising a core surrounded by a permeable membrane wherein the outer surface of the core and the inner surface of the permeable membrane define a boundary for a zone in which cells may be contained. The maximum distance between the outer core surface and the permeable membrane is sufficiently narrow to provide conditions suitable for survival and function of the contained cells, whereby the viability of a large proportion of the contained cell mass is supported. Preferably the core is substantially cell-free.

In one embodiment of the invention, a device for providing substances derived from cells contained in the device comprises a core having a an interior region and an outer boundary surrounding the interior region. A zone for containing cells substantially surrounds the core and extends from the outer boundary of the core to an inside surface of a permeable membrane. The permeable membrane has inside and outside surfaces. The distance from the outer boundary of the core to the inside surface of the permeable membrane is sufficiently thin to support the viability of cells in a cell layer located closest to the outer boundary of the core and most distant from the inner surface of the permeable membrane.

In another embodiment, the distance from outer boundary of the core to the inside surface of the permeable membrane is defined by a diffusion length parameter of less than about 500 microns.

In another embodiment, the core and the permeable membrane are proportioned such that a diffusion length parameter (DLP), which is measured on a cross-section of the device taken perpendicular to a long axis of the core and passing through the core, cell zone and permeable membrane at a point along the long axis of the core where the cell zone is sufficiently thick to contain at least one cell layer, is less than about 500 microns. The DLP is defined as the ratio of the total area of cell zone of the cross-section divided by the perimeter of the cell zone. The perimeter of the cell zone is defined as the length of the permeable membrane of the cross-section.

The devices may be implanted directly into a host to provide substances produced by the cells contained within the device.

In a preferred embodiment of this invention an internal core is provided in the device which allows for a greater number of viable cells to be maintained within the device than would be possible if the core were absent from the device.

The device of this invention also provides for a more rapid rise to a plateau level of released substances by decreasing the transport delay of environmental stimuli to the cells, and by decreasing the corresponding delay associated with diffusion of therapeutic substances out of the device.

In another embodiment of this invention, a method of treating patients in need of supplemental or replacement therapy is provided by implanting into such individuals the devices of this invention containing cells capable of providing therapeutic substances.

Another embodiment of this invention provides a surface within the zone for containing cells which increases the number of attachment sites for the support of anchorage dependent cells.

This invention also provides a method of producing the cell containing devices. This method comprises providing an exterior membrane comprising a lumen wherein the membrane is impermeable to cells but permeable to both nutrients and the therapeutic substance produced by the cells. The method further comprises providing a cell displacing core and introducing the core into the lumen of the membrane to create a zone for maintaining cells. The zone for maintaining cells is defined by the surface of the core and the inner surface of the membrane. Cells are introduced into the zone for maintaining cells and the membrane is sealed so as to contain the core and cells within the device.

Another embodiment of this invention provides a method of separating cells from a bioreactor to facilitate the purification of cell products.

An object of this invention is to provide an implantable device which maintains cells in a viable state.

Another object of this invention is to provide devices having a space filling core which enables a greater number of viable cells to be contained within the total volume occupied by a cell encapsulation device.

DETAILED DESCRIPTION OF THE INVENTION

Figure 1A:
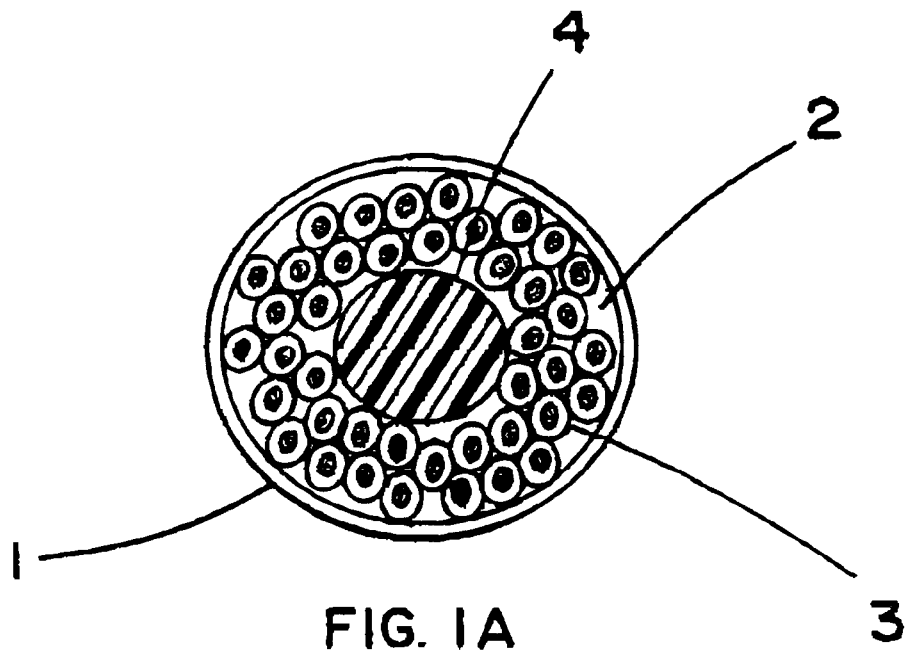
FIGS. 1A and 1B. Transverse (1A) and longitudinal (1B) cross-sectional diagram of cylindrical device with a core illustrating the permeable membrane (1), the zone for sustaining cells (2), cells (3), core (4), and constrictive seals (5).
Figure 1B:
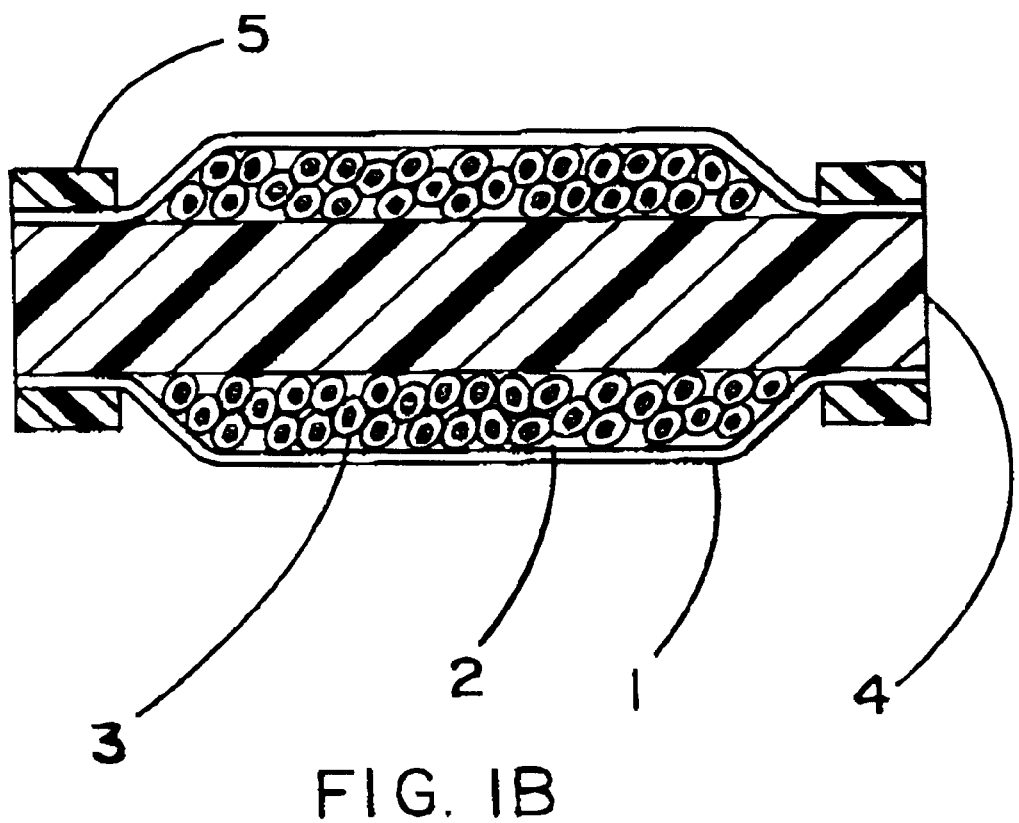

The devices of this invention are comprised of a core surrounded by a permeable membrane and a space bounded by the core outer surface and the permeable membrane inner surface. The space in between the core and the permeable membrane is a zone capable of maintaining cells. The device may have any geometry which allows for the maintenance of the core-space-permeable membrane relationship. This geometry may include but is not limited to spheres, cylinders or sheets. Cylinders and spheres are preferred. Most preferred are devices wherein the permeable membrane and the core are both cylindrical having longitudinal axes which are substantially parallel to each other. FIGS. 1A and 1B illustrate a cylindrical device of the invention and shows the permeable membrane (1) surrounding the device, the zone (2) for containing cells (3), and the core (4).

Cells contained within the devices of this invention obtain nutrients from the environment outside the device. The devices of this invention provide greater exchange of nutrients and wastes between the cells within the device and the external environment by locating the cell mass in close proximity to the permeable membrane in contact with the outer environment. This close proximity of cells to the permeable membrane is achieved by displacing cells from the inner portions of the device by the presence of the core.

The core of the device is inert in that it is not primarily intended or required to provide diffusible nutrients to be used by the cells in the device. Although the core is not primarily designed to supply nutrients, it may be treated to provide a surface which promotes adhesion or provide substances which promote the survival, growth, or function of the cells providing therapeutic cell products. Preferably, such cell promoting substances are adsorbed on the outer surface of the core. Collagen, poly-L-lysine, laminin, fibronectin, and porous PTFE are among the substances which may be adsorbed to the core to promote cell growth and/or functions. In addition, the core may have an outer porous layer which serves as a matrix for attachment and maintenance of anchorage dependent cells.

The cores of the device of the invention may be considered to have an interior region and an outer boundary surrounding the interior region. Different regions of the core may have the same or different porosities and may be porous or nonporous. However, the porosity of the core should prevent the migration of cells into the interior region of the core which should be substantially cell-free.

Figure 2:
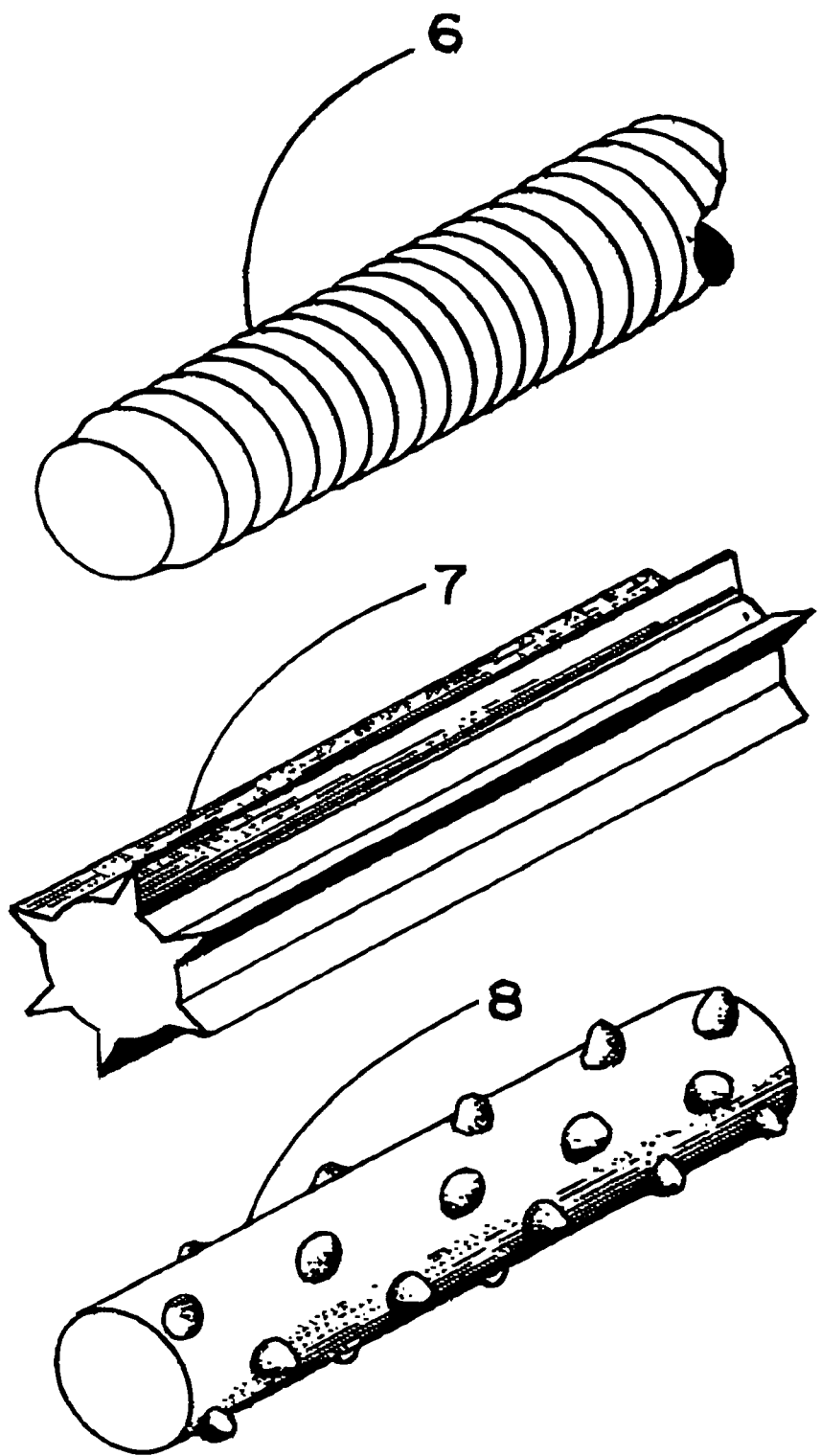
FIG. 2. Diagram of cylindrical devices including coils (6), longitudinal ridges (7), and bumps (8) which act to center the core within the permeable membrane.

Besides displacing cells from the interior of the device, the core also serves to provide rigidity to the device which facilitates manipulation during manufacture and implantation and retrieval by the health care provider. The core may be any shape. In one embodiment, the shape of the core is substantially the same as that of the permeable membrane. In another embodiment, the core may be spherical or cylindrical with protrusions extending out from the core surface. These protrusions, for example, and as illustrated in FIG. 2, may be coils (6), ridges (7), or bumps (8). The height of each protrusion may be designed to define the minimum space in between the core surface and the permeable membrane inner surface and may aid to center the core within the device.

Figure 3:
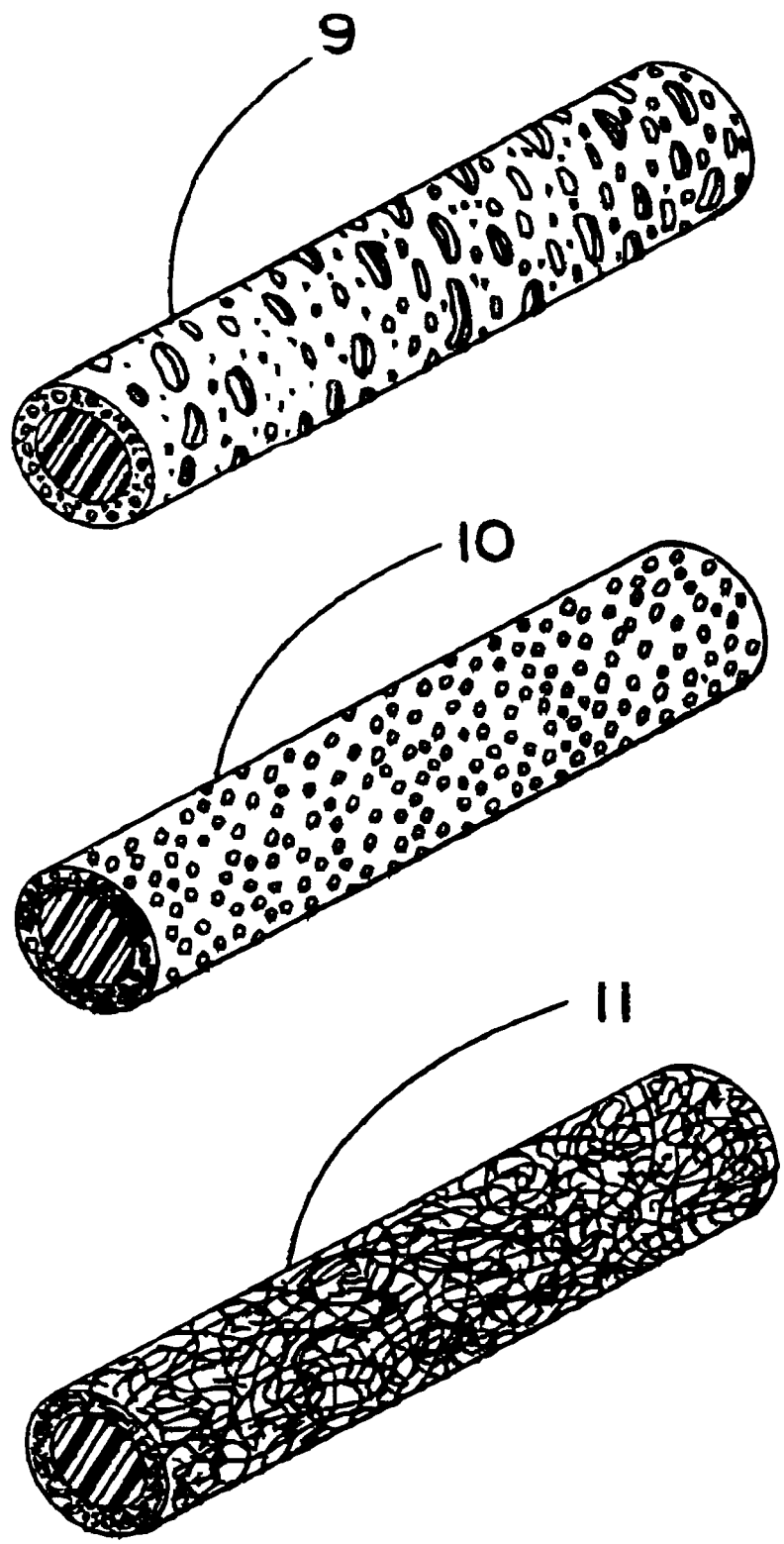
FIG. 3. Diagram of cylindrical device including the following surfaces surrounding the core to provide an increase in the number of surface sites available for attachment by anchorage dependent cells: a microporous expanded polytetrafluoroethylene (PTFE) (9), an aggregation of cell culture microspheres (10), and a fibrous matte (11).

The space bounded by the core and the permeable membrane, optionally may contain substances to promote cell growth. Such substances may include material to provide a support on which anchorage dependent cells may adhere. Preferably, a porous network is provided throughout the space provided for cell growth in between the core and the permeable membrane. Suitable material for the support are solids including but not limited to expanded or porous PTFE, dextran, collagen, polyester, polystyrene and other natural or synthetic polymers which promote cell attachment. The support may be present in the cell zone in various forms including, among others, random or trabecular networks, microspheres and fibrous mattes. FIG. 3 illustrates examples of solid supports such as microporous expanded PTFE (9), an aggregation of cell culture microspheres (10), and a fibrous matte (11). The solid support in the cell zone may also contribute strength to the device and aid in maintaining the shape of the device.

In a preferred embodiment, the geometry of the device maintains the viability of cells in contact with, or in close proximity to the core. Cell viability may be assessed using various indicators of cell function. For example, the ability of cells to exclude certain dyes, such as trypan blue, which accumulate in dead cells may be used to assess cell viability. Evidence of cell viability may also be based on assessments of basal metabolism or cell proliferation. The demonstration of synthesis of cell products is also indicative of cell viability. A conclusion of cell viability may be based on the detection of any one indicator of cell viability.

Cell viability may be assessed prior to or after implantation. However, it is preferred to assess viability prior to implantation because of the potential for interactions between the device and the environment which compromise cell viability in a manner which is unrelated to the geometry of the device.

In a preferred method of assessing cell viability, the device containing cells is cultured in vitro for a period of time sufficient to allow the population of cells to reach a plateau or steady state. The medium for culturing the device should contain sufficient concentrations of nutrients to maintain the viability of the number of cells at the plateau level if such cells were grown in culture without the device. In addition, the medium should be sufficiently replenished to avoid cell death due to depletion of nutrients from the medium outside the device. Evidence of having reached a plateau may be based on a stable metabolic rate.

To assess cell viability in the device, the number of viable cells most distant from the permeable membrane and forming a perimeter surrounding the substantially cell-free core is determined. The perimeter of cells which are assessed for viability will be essentially the first cell layer surrounding the substantially cell-free region of the core. Preferably, at least about 10% of the cells in the first cell layer will be viable. More preferably, at least about 50% of the cells in the first cell layer will be viable. Most preferably, at least 80% of the cells in the first cell layer will be viable.

If a vital dye is to be used to assess viability, the dye is added to the culture medium, or injected directly into the cell space of the device, when the number of cells has reached a plateau. To assess cell viability, the device is removed from the medium after a sufficient time to allow the dye to diffuse into the device, the device is cross-sectioned, and the number of viable cells in the first cell layer surrounding the core is determined as described above.

Another method of assessing viability may consist of pulsing the cells at the plateau phase with a radioactive precursor for a metabolic product and determining the percent of cells in the first cell layer which incorporate the precursor into a product. Autoradiography may be used to localize the radioactive product. Because the radioactive precursor and the product may be present in the same vicinity, the analysis may be done in conjunction with immunolabelling of the newly synthesized cell products.

Figure 4:
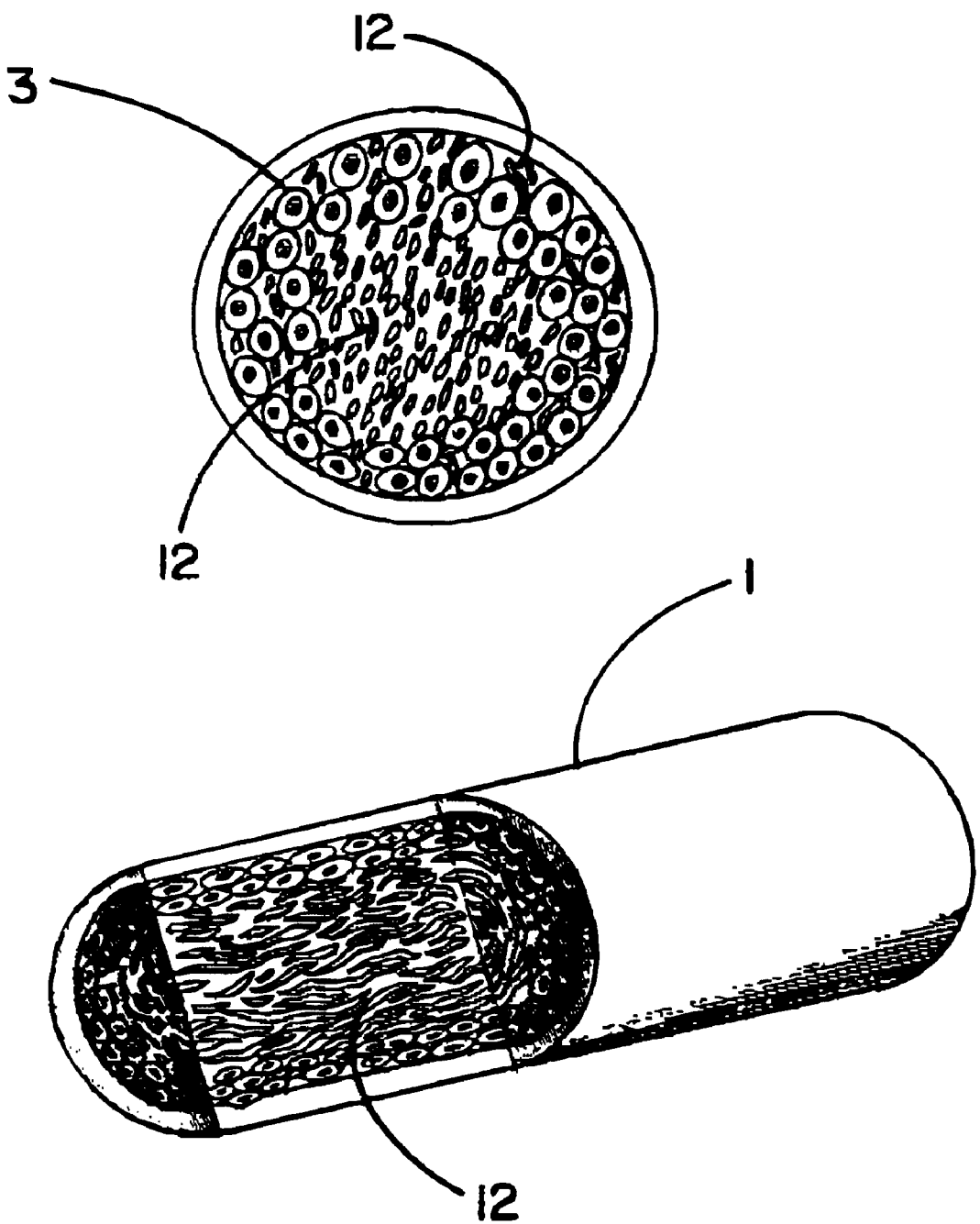
FIG. 4. Diagram of cylindrical device wherein core material (12) is distributed throughout the volume enclosed by the permeable membrane (1), and wherein cells (3) populate the more peripheral spaces provided in the core material.

The first cell layer closest to the core may be irregular in shape due to the core geometry or the substance used as the core material. In addition, and as illustrated in FIG. 4, the core material may be comprised of the same material used to provide a support for cells in the cell zone. If the core material is the same material as present in the cell zone, the porosity of the material comprising the core preferably should be such as to prevent cells migrating to a distance from the permeable membrane where they will not receive sufficient nutrition to remain viable.

Another parameter for determining dimensions of the preferred devices of the invention is the diffusion length parameter (hereinafter, "DLP") which is proportional to the thickness of the zone for maintaining cells. DLP is determined by taking a planar section through the device, where such section is taken perpendicular to a longest axis of the device and passes through the core, the permeable membrane, and the cell zone at a point sufficiently thick to contain at least a single layer of cells. The total area available for cells between the substantially cell-free region of the core and the inner perimeter of the permeable membrane is determined from direct or microscopic observations. DLP is then calculated by dividing the total area available for cells by the length of the inner perimeter of the permeable membrane. In calculating the DLP for devices containing cell displacing substances in the cell zone such as a solid support, the entire area of the cell zone is used to calculate DLP, without subtracting the area occupied by the support.

Standard methods may be used to determine the area between the core and the permeable membrane available for cells. In one method, the planar cross-section of the device is photographed. The area for cell growth is then cut out and weighed. To determine the area, the resultant weight is then divided by the average weight per unit area of the photographic paper, and scaled by the appropriate magnification factor of the microscope and camera.

DLP values are preferably less than about 500 microns. More preferably, DLP values range from about 25 to 250 microns, and most preferably from about 50 to 100 microns.

Preferably, the thickness of the cell zone and the corresponding DLP value is inversely proportional to the square root of the metabolic activity of the cells to be contained within the device. In addition, the thickness and DLP values are directly proportional to the square root of the concentration difference between available nutrients and concentrations of nutrients required for survival. Accordingly, these relationships may be used to design devices of various geometries which are particularly well suited for use with a particular cell type.

By determining a preferred geometry for one cell type, other devices may be constructed for other cell types by comparing the metabolic activities of the cells and modifying the design in accordance with the relationships described above. For cells having a metabolic rate, of about 1 mg glucose/(ml of cells·min) in a medium containing glucose at 5 mg/100 ml, the most preferred DLP value ranges from about 50 to 100 microns. Preferably, oxygen consumption would be used to design devices having preferred geometries. For example, the preferred DLP range for cells utilizing oxygen at a rate of about $4.6 \times 10^8$ moles oxygen/(ml of cells·sec) is also about 50 to 100 microns. (Values for glucose and oxygen consumption are based on a cell volume of 2000 femtoliters/cell.) This value assumes the diffusion coefficient of oxygen in culture medium to approximate that of water, the partial pressure of oxygen to be 120 mm of mercury, and that the permeable membrane contributes negligible resistance to the diffusion of nutrients.

Although the presence of any core will provide the advantage of increasing the proportion of cells near the permeable membrane, the preferred devices have cores which increase the number of cells which may be packed in a given volume compared to devices without cores. In devices without cores, larger diffusion distances result in lower concentration gradients, which in turn result in lower net flux of nutrients and lower capacity for viable cells.

In addition, cells in the interior of the device which do not receive enough nutrients may die and release substances toxic to the cells in closer proximity to the permeable membrane thereby causing the death of even a greater number of cells. Accordingly, a greater number of cells may be viable in the annular space or zone created in between the outer core surface and the internal surface of the permeable membrane than would otherwise be viable if the core was not present. A limit will be reached where increasing the core size no longer improves viability, and simply displaces viable cells.

A core of any size which displaces cells from the central portion of the device is suitable for use in the devices of this invention. Preferably, the core occupies sufficient volume to limit the diffusion length parameter (DLP) of the device to a value less than or equal to the maximum thickness to which a given cell mass can be sustained by diffusion through a given permeable membrane.

The maximum thickness will depend on several factors including the metabolic rate of the cells, packing efficiency of the cells, permeability characteristics of the permeable membrane and the cell mass, the nutritive content of the surrounding medium, and any volume displaced by a porous cell growth substrate. Preferred values of maximum thickness for a dense cell mass in which the volume of the zone available for cells is maximally packed with cells based on the cell volume, range from about 50 to 100 microns for pancreatic cells and cells having similar metabolic rates and thus similar nutritional requirements, to about 500 microns for cells which are present in dilute suspension or which have low metabolic demand. The maximum thickness values will be relatively small, less than about ten microns, in the case where the metabolic demand of the cell is high or where nutrients are scarce due to unfavorable environmental conditions or poor membrane permeability.

As discussed above, to determine the preferred dimensions of the device it may be necessary to first determine the consumption requirements for certain critical nutrients, for example oxygen or glucose. Methods of determining oxygen and glucose consumption rates are well known to those skilled in the art and are commercially available. From the determinations of the minimal conditions necessary to maintain the cells in an adequate state of nourishment device geometry may be optimized.

Fick's second law of diffusion may be applied to the design of the devices of the invention. Using a cylindrical device as an example, it can be shown that introducing a core that is 90% of the permeable membrane radial dimension remarkably increases the linear carrying capacity of a coreless device tenfold. These devices of the invention have several advantages over coreless devices. By increasing the size of the device, the diameter of the device becomes larger and easier to manipulate. For a given cell capacity, the estimated length can decrease further easing manipulation. Ease of manipulation will be improved during all device handling steps, including manufacture, storage, implantation, and ultimately retrieval.

In a preferred embodiment, a cylindrical device is provided with an annular cell zone defined as the space between the inner surface of the permeable membrane and the outer surface of the core material, such that the average distance between the two surfaces is less than about 500 microns. More preferably the space between the core and the inner surface of the permeable membrane averages about 25 to 250 microns. Most preferably, the space between the core and the permeable membrane averages about 50 to 100 microns.

An empirical method for optimizing the core size for a given device is to build several devices of varying core dimension, culture the devices in their intended environment or analogous medium, and choose the device which provides the greatest steady state mass of viable cells. Alternatively, the device may be optimized by selecting a core which results in the greatest production of therapeutic substance. In addition, devices of a desired diameter may be constructed without a core, filled with cells and cultured to obtain a constant cell mass. If a necrotic cell mass is observed upon inspection of the device after it has been cultured for a sufficient length of time, a device may then be produced containing a core. Preferably, the core diameter is about equal to, or greater than, the diameter of the necrotic cell mass.

A further advantage of the devices of this invention is the improved strength of the device. Devices without a core derive all of their strength from the encapsulating membrane. Long coreless devices which must be thin in order to maintain cell viability require thicker membranes to provide sufficient strength. Increasing membrane thickness also increases resistance to diffusion, and therefore decreases the number of viable cells which can be contained within the device. The presence of a core in the devices of this invention provide the ability to add significant strength to the device without increasing membrane thickness.

Another advantage provided by the presence of the core is a more rapid response to environmental stimuli by the cells contained within the device. Because the core requires the cells to reside close to the encapsulating membrane, the distance and thus the time required for transient diffusion to occur to the cells is reduced. This increase in speed is valuable in the case where the therapeutic cells function by responding to a chemical signal such as a changing concentrating of a physiologic substance. The faster the signalling substance can diffuse to the cells, and the faster the therapeutic product can diffuse out of the device, the better the device performs.

Any material which acts to displace cells from the space defined by the perimeter of the permeable membrane is suitable for use as the core material. Suitable core materials may include but are not limited to porous or expanded polytetrafluoroethylene, polydimethysiloxane, polyurethane, polyester, polyamide, or hydrogels derived from polysaccharides, alginate or hydrophilic polyacrylonitrile such as Hypan®. The core is preferably a flexible polymer or elastomer. More preferably, the core may be manufactured from polysaccharides, hydrophilic copolymers of polyacrylonitrile, or other polymer components. Most preferably, core compositions such as Hypane comprise a copolymer of polyacrylonitrile and acrylamide. When hydrogel such as Hypan® is used the water content of the hydrated gel should be sufficient to provide flexibility while not exceeding a water content which allows cells to enter the core. Preferably, the gel comprising the cores is hydrated to between 35 and 95%. Most preferably, the water content is about 68%. Further details of the preferred core composition and the method of manufacturing the core materials are disclosed in the art, such as, U.S. Pat. Nos. 4,379,874, 4,420,589 and 4,943,618 which are incorporated herein by reference. Reaction conditions are chosen which provide a 38% conversion of acrylonitrile groups to acrylamide.

Manufacture of the core may be by any method known to those skilled in the art of manufacturing polymer structures. The core is preferably formed as a cylindrical rod by extruding the polymer through a round die. Preferably the core diameter when it is a cylinder is between about 0.2 to 10 mm. More preferably the core diameter is about 1.5 mm.

The permeable membrane may be manufactured from any biologically compatible material having the appropriate permeability characteristics. The permeable membrane should permit the passage therethrough of cellular nutrients, waste products, and therapeutic substances secreted by cells contained within the device. The permeable membrane should not allow the passage of cells and viruses. Preferably, the permeable membrane should serve to isolate the cells contained within the device from recognition and attack by cellular components of the host immune system. More preferably, the permeable membrane should serve to isolate the cells contained within the device from contact with molecules of the host immune system which function to recognize foreign cells, to direct an attack against such foreign cells, or to directly exert toxic effects against foreign cells.

Examples of polymers having suitable selective permeability properties and which may be used as the permeable membrane may be selected from the group consisting of sodium alginate polyhydrate, cellulose acetate, panvinyl copolymers, chitosan alginate, polyacrylates such as Eudragit RL® manufactured by Rohm & Haas, GmbH, agarose, acrylonitrile, sodium methylyl-sulphonate, polyvinyl acrylates such as those available as XM50 available from W. R. Grace and Co., and porous PTFE.

Most preferably the permeable membrane is prepared from a polyacrylonitrile copolymer of the type described in U.S. Pat. Nos. 4,379,874, 4,420,589 and 4,943,618 which are incorporated herein by reference.

In a preferred embodiment, the permeable membrane is a hydrogel such as that available from Kingston Technologies Inc. and sold under the tradename Hypan®. Preferably the hydrogel suitable for the permeable membrane has a water content of between about 35 and 95. Most preferably the water content of the hydrogel is about 68%.

Manufacture of the permeable membranes is also preferably accomplished by extruding the polymer through a die wherein a hollow tube is formed having the appropriate dimensions. The extruded polymer, which serves as the permeable membrane, should be of sufficient diameter to allow the insertion of the core into the permeable membrane.

Extrusion of the polymer material to prepare the permeable membrane is accomplished using standard extrusion techniques. To prepare the permeable membranes for making the devices of this invention, polymer material is dissolved in a suitable solvent to result in a solution of sufficiently low viscosity to allow the solution to be extruded through a thin walled annular die orifice. Preferably, the annular orifice is formed from a die having a 0.105 inch O.D. and a 0.095 inch I.D. to produce a tube of permeable membrane having a lumen of the desired size. Polymer solution may be fed through the die with a controlled flow rate using a syringe pump. Coagulation of the polymer solution may be achieved by having the die immersed in a coagulation bath of room temperature deionized water. Coagulation of the polymer solution occurs upon contact with the water at the die exit. The resulting solidified tube may be taken up by speed controlled capstan rollers and a storage spool. Tubing is then rinsed of residual solvent and stored immersed in water.

Preferably, very thin walled tubing is obtained. This may be accomplished by selecting a take up speed which exceeds the rate at which tubing exits the die to cause tube stretching. The die exit velocity is calculated by dividing the polymer feed rate by the die annulus cross sectional area.

The wall thickness of the permeable membrane is of a thickness which permits the passage of nutrients and waste products and. allows for the viability of the cells contained within the device. Preferably the thickness of the permeable membrane is between 2 and 100 microns. More preferably the thickness is between about 5 and 50 microns. Most preferably the thickness is between 15 and 25 microns.

The permeable membrane should have a molecular weight cut off (MWCO) range sufficient to prevent cells from moving into or out of the device but large enough to allow the passage of nutrients, wastes and therapeutic substances secreted by cells contained within the device. The precise MWCO range will vary depending on the membrane material, type of cells contained within the device and the size of the therapeutic cell product to be released into the surrounding environment. Accordingly permeable membranes having a MWCO of between 10 kD to 2000 kD may be suitable for use with the devices of this inventions. A MWCO range of between 30 kD and 150 kD is particularly preferred in applications where it is desired to isolate the contained cells from contact with molecules of the immune system capable of recognizing or destroying the contained cells.

In a preferred method of manufacturing a device of this invention a core and permeable membrane are separately prepared and the lumen of the permeable membrane is expanded with liquid or gas to allow for the insertion of the core component. Once the core is inserted into the lumen of the permeable membrane various methods may be used to seal the device.

The core may be inserted into the permeable membrane before or after the device is inoculated with cells. Cores may be loaded into the permeable membranes incompletely hydrated or swelled. In a preferred method of preparing the device a substantially dry, or incompletely hydrated core is inserted into the lumen of the permeable membrane. Cells may be added before, with or after the insertion of the core. After sealing the device, the device is placed in an environment that allows the core to swell to the appropriate size. In another method of preparing the devices of the invention, cells are prepared in a slurry comprising cells, media and a hydrated Hypan® core. This slurry is then injected into the permeable membrane which has been previously cannulated with a stainless steel tubing and sterilized. Once the core is located inside the tubing, the stainless steel tube is removed and the ends are sealed. The ends may be sealed with surgical ligatures clips or by other suitable means. In a preferred embodiment, a short length of biocompatible tubing is placed over the ends of the device to provide a constrictive seal. FIG. 1B illustrates constrictive seals (5) which seal the permeable membrane to the core. Such seals may be made of substances such as silicone rubber or PTFE. Sealing of the ends may also be accomplished by allowing the core to swell into a restrictive collar.

The devices of this invention provide a source of therapeutic substance by virtue of the ability of the cells within the encapsulating device to manufacture and secrete such therapeutic substances. Accordingly, the device should contain a sufficient number of cells to provide a therapeutically effective amount of substance. The advantage of the geometry of the devices of this invention is that the presence of the core material increases the proportion of cells in proximity to the permeable membrane. This increased proximity reduces the proportion of cells which do not receive sufficient nutrients because of their distance from the permeable membrane.

Another advantage of the devices of this invention is that cells can be encapsulated in a manageable device such that the cells are in sufficient quantity to provide therapeutic amounts of cell products and are sufficiently close to the permeable membrane to avoid deleterious effects of cell necrosis which may occur if the diameter of the permeable membrane is so large that the cells in the inner portions of the device are not able to exchange nutrients and waste. This invention. avoids such effects by the presence of a volume displacing core contained within the permeable membrane which effectively prevents cells from becoming too distant from the permeable membrane surface. An added advantage of this configuration is that the device is kept sufficiently large to be easily manipulated during implantation and removal.

Various types of prokaryotic and eukaryotic cells may be used with the devices of this invention. Preferably the cells secrete a therapeutically useful substance. Such substances may be hormones, growth factors, trophic factors, neurotransmitters lymphokines, antibodies or other cell products which provide a therapeutic benefit to the device recipient. Examples of such therapeutic cell products include but are not limited to insulin, nerve growth factor, interleukins, parathyroid hormone, erythropoietin, albumin, transferrin, and Factor VIII.

The devices of this invention may be used to provide trophic substances to treat various neurodegenerative disorders. Such factors include but are not limited to nerve growth factor (NGF), and other members of the NGF gene family including brain derived neurotrophic factor, neurotrophin-3 and neurotrophin-4; ciliary neurotrophic factor; and basic fibroblast growth factor.

Cells such as PC12 pheochromocytoma cells may be implanted in the devices of the invention to provide neurotransmitters such as dopamine to provide therapy for Parkinson's disease. Cells providing other neurotransmitters may be used as well.

Those skilled in the art will recognize the wide variety of cell products useful for treating various disorders which may be produced by the cells used to seed the devices of this invention. PCT application W092/19195 of Dionne published Nov. 12, 1992, which is incorporated herein by reference, describes various cell types suitable for use with immunoisolating devices and their application.

Cells which have been genetically altered to contain at least one additional nucleic acid sequence related to the expression of a therapeutic substance may be particularly useful to be included in the cell zone of the devices of this invention. These genetically altered cells are distinguishable from naturally occurring cells which do not contain the additional nucleic acid sequence. The additional nucleic acid sequences may be heterologous or homologous to the cells expressing the therapeutic substance. In addition, the additional nucleic acid sequences may code for the therapeutic substance itself and/or comprise non-coding sequences, e.g. regulatory or antisense sequences which modify the expression of endogenous genes. Among the forms of nucleic acid sequences which may be useful for having been inserted into the genetically altered cells are intronless coding sequences (i.e. cDNA), copies of genomic genes, and regulatory sequences. The additional nucleic acid sequences may be comprised of sequences obtained from other cells, viruses, or synthetic sequences.

The size of the device to be implanted will vary depending on the number of cells necessary to provide sufficient amounts of therapeutic substances and the location of the device. Preferably, the device to be implanted in a human would be cylindrical and have an overall length of between about 0.5 cm to about 3 meters. Multiple devices may be implanted in a single individual.

Devices may be implanted anywhere in the recipient which allow the device to receive the necessary environmental stimuli to respond by releasing therapeutic substances and which provide the necessary nutrients to maintain the viability of cells within the device. Suitable locations for implanting devices include but are not limited to the peritoneal cavity, cerebral ventricles or inside blood vessels. Devices may also be located subcutaneously or intramuscularly.

To treat individuals in need of treatment in accordance with the method of this invention, at least one device of the invention is seeded with cells which will provide the necessary therapeutic substance. After establishing the device in culture, the device is transferred into the individual in need of treatment. As discussed above, the devices may be inserted in various sites throughout the body, by means such as intravascular suspension, subcutaneous or intraperitoneal insertion, through procedures now known or later developed.

Sufficient numbers of cells are inserted into an individual to produce therapeutically effective amounts of the therapeutic substance. One or more devices may be used to achieve the requisite number of cells. The amount of therapeutic substance produced by the cell containing device may be estimated based on the production of the therapeutic substance by the device in tissue culture outside the individual. Based on such in vitro measurements, the correct size and number of devices containing the appropriate number of cells may be determined.

The devices of this invention may also be used to prepare cell products-such as therapeutic substances. For such applications, the devices of the invention are seeded with cells and cultured in vitro for a sufficient time to allow for cell products to diffuse out of the device and into the cell medium surrounding the device. The therapeutic substances may then be isolated from the culture medium without being contaminated with cells. Having the cells contained within an easily removable device facilitates substance purification by eliminating the burden of procedures necessary to remove cellular components from the culture medium.

EXAMPLE 1

Devices were made and tested with cells in vitro to demonstrate, that a stable viable cell population could be achieved.

A. Extrusion of Tubular Membrane

Hypan® tubing (HN-68 obtained from Kingston Technologies, Inc.) for use as the permeable membrane was prepared by dissolving polymer (10% w/w) in a solvent consisting of an aqueous solution of 55% NaSCN resulting in a polymer solution of sufficiently low viscosity to be extruded through a thin walled annular die orifice. Using a syringe pump, the polymer solution was fed through a die at a controlled flow rate of 10 ml per hr. The die used for producing the permeable membrane consisted of a 0.105 inch OD, 0.095 inch I.D. annular opening and was immersed in a coagulation bath consisting of room temperature deionized water. Coagulation of the polymer solution occurs upon contact of the polymer with the water at the exit of the die. The resulting solidified tube was taken up by capstan rollers at a controlled speed of 3.5 feet per minute and the tubing was rinsed of any residual solvent. The resulting tubing was stored immersed. in water. Stretching the tube as it coagulated by the above takeup speed resulted in very thin walled tubing. The resulting permeable membrane was measured to have an outside diameter of 1.95 mm and a wall thickness of 15 microns.

A Hypan® core of HN68 was extruded with a resulting diameter of 1.5 mm.

B. Seeding the Device with Cells

CGT-6 cells, a genetically engineered murine cell line described in Hughes SD et al. *Proc. Natl. Acad. Sci.*, USA; 89:688–692 (1992), grown to confluency in T75 flasks, were prepared for seeding into the device. Cells were trypsinized, centrifuged and resuspended in 5 ml of medium (DMEM containing 450 mg/dl of glucose). A slurry consisting of cells, media, and hydrated Hypan® core was injected into five lengths of Hypan® tubing each of which had been precannulated with a length of stainless steel tubing and steam sterilized. Once the core was located inside the tubing, the ends of the tubes were sealed with surgical ligating clips, padded by a small square of silicone rubber. The five devices were each placed in a separate well of a 6 well tissue culture plate. Unloaded cells were placed in the sixth well to determine the viability of this population of cells after the loading procedure. All wells were filled with 4, ml of 450 mg/dl glucose growth medium. The medium was replaced every day with fresh medium. The exhausted medium from each well was retained and frozen for subsequent analysis. An estimate of the population of the devices was determined by measuring the glucose consumption. Previous experiments determined that 1 million CGT-6 cells consumed glucose at a rate of 3 mg/day.

Devices were seeded with cells at day zero and glucose consumption was continuously monitored through day 83. Between day 83 and day 114, the medium continued to be changed although less frequently and glucose consumption was not measured. At day 114, the devices were removed from the medium, examined, measured and the cells harvested. Harvested cells were treated with trypsin and counted using a Coulter counter.

Immediately after seeding the devices with cells, the devices had a uniformly milky appearance. Within one day and for approximately 3 weeks thereafter, the cells colonized the lowest part of the device to form a line of agglomerated cells parallel to the length of the device. Over time, the cell number increased until the cells were confluent and the cells appeared to have grown around the core completely occupying the annular space formed between the core and the permeable membrane. In the final months of culture, the devices appeared fully packed, having a superconfluent appearance. Although the core was obscured from view, its outline could be approximated at the center of the cell mass.

Due to the presence of cells outside of the device, some of which adhered to the silicone rubber pads, the devices were rinsed daily to remove cells not contained within the device. After the rinses, the devices contained a large superconfluent cell mass with trace clumps of cells observed on the silicone pads.

Measurements of the device dimensions were determined from photomicrographs taken of the devices immediately prior to harvesting. Table 1 shows the dimensions of the five devices. Precise measurements were not obtained for device no. 5 which did not photograph with sufficient clarity to allow for length determinations.

TABLE 1

| Device # | Approximate Diameter | Approximate Length |
|---|---|---|
| 1 | 1.8 mm | 22.9 mm |
| 2 | 1.8 | 22.0 |
| 3 | 1.67 | 31.5 |
| 4 | 1.67 | 18.5 |
| 5 | 1.47 | >12.8 (length uncertain) |

Figure 5:
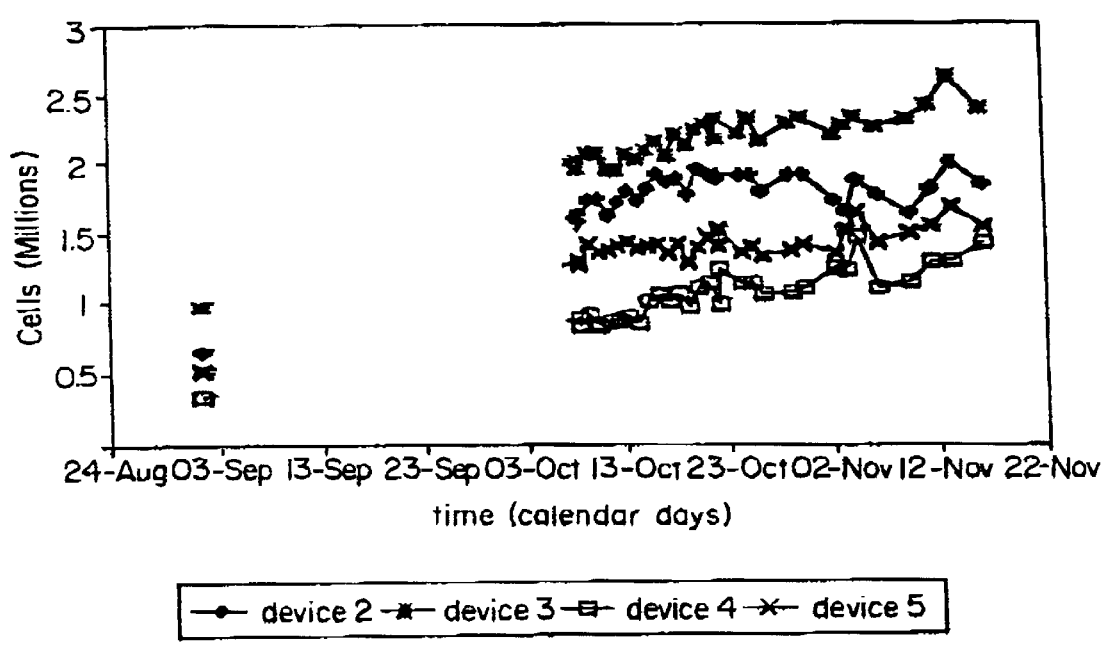
FIG. 5. Graphical illustration of the increase in cell population over time for four devices (labelled+, *, □ and x, respectively), seeded with CGT-6 cells. Cell number is based on measurements of glucose consumption. Data from a first device is omitted because that device was cultured under non-standard conditions.

FIG. 5 shows the relationship between days in culture and glucose consumption. Data between day 1 and day 43 is omitted because cells were found to be present in the medium outside the device and contributed significantly to glucose consumption. An increase in the glucose consumption over time up to a plateau level was observed in all of the devices tested.

Viability and cell number for the five devices at the termination of the experiment (114 days in culture) is shown in Table 2. Viability for the five devices averaged about 85% with cell numbers ranging from $5.4 \times 10^5$ to $1.6 \times 10^6$ cells per device.

TABLE 2

| Device # | Approximate Cell Number (x $10^6$) | Viability (%) |
|---|---|---|
| 1 | 1.6 | 80 |
| 2 | 0.94 | 89 |
| 3 | 1.3 | 89 |

TABLE 2-continued

| Device # | Approximate Cell Number (× 10⁶) | Viability (%) |
| --- | --- | --- |
| 4 | 0.54 | 84 |
| 5 | 0.81 | 84 |

EXAMPLE 2

Another encapsulation device produced to demonstrate viability was constructed utilizing a thin walled (15 micron) tubular permeable membrane with an external diameter of 1.95 mm constructed of a polyacrylonitrile-acrylate copolymer as described in U.S. Pat. No. Nos. 4, 943, 618, 4,379, 874 and 4,420,589. This device was prepared by injecting into the permeable membrane a liquid slurry comprising a suspended quantity of viable CGT-6 cells and a porous PTFE space filling core 2.5 cm in length and 1.75 mm in diameter. The ends of the device were sealed using standard surgical ligating clips with a small (5 mm×5 mm) square of silicon rubber used to augment the clip function by limiting stress on the tube membrane.

The CGT-6 cells were prepared for slurry injection into the device using trypsin, followed by centrifugation and resuspension in cell culture media.

Immediately following assembly, the device was placed in a tissue culture well of a 6 well plate, immersed in 4 ml media and incubated under standard conditions appropriate for the cells in free culture. The initial appearance of the device was translucent. Suspended cells were observable through the clear permeable membrane.

Within one day, the cell slurry had settled to form a curvilinear agglomeration approximately defined by the lowest portion of the device as it lay in the cell culture well. Over the next three weeks, this conformation changed as the cell colony multiplied and occupied larger areas of the annular space, forming a translucent amorphous mass.

Glucose uptake was measured as an indication of cell viability and proliferation of cells in the device using the same conversion factor described in Example 1. Glucose uptake was measured as the difference between glucose levels measured in the media surrounding the device over a 24 hour period, and the glucose level in a control well. Glucose uptake of the device was initially low, and increased over the term of the device until it stabilized at a level which corresponded to the presence of $2 \times 10^6$ cells in free culture. Insulin production of the device during the period when the device population was stable was consistent with a population of $2 \times 10^6$ cells.

At many times during the culture of this device it was necessary to manipulate the device in an aseptic manner with surgical instruments. This handling consisted of grasping the device with forceps, bathing it with a stream of media, and placing it into another container.

A final evaluation of this device was performed after a term of 56 days. The intact device was treated with a viability stain which stained living cells a green color and dead cells a red color ("Live/Dead TM Viability/cytotoxicity assay, Molecular Probes Inc.). Subsequent gross examination of the stained device revealed a high degree of viability as indicated by a generally green hue. After evaluation of the intact device the device was cut opened and the cells were prepared for Coulter counting by trypsinization. Viability was also evaluated. Cell counts of $1.8 \times 10^6$ cells obtained from the Coulter counter substantially agreed with the $2 \times 10^6$ cells estimated from the glucose uptake estimates. Cell viability was determined to be 82%.

EXAMPLE 3

Another device having the following dimensions was constructed essentially as described in Example 1:

permeable membrane inner radius: 800 microns core outer radius: 725 microns permeable membrane thickness: 25 microns This device was seeded with approximately $1.4-10^6$ cells and was cultured for 51 days with daily media changes. The number of cells present in the device after 51 days was estimated at $1.6-10^6$ cells based on daily glucose consumption measured in the media.

EXAMPLE 4

Four devices similar to those described in Example 3 were prepared for implantation into dogs.

To specifically adapt the devices for implantation into the vascular system, a small bullet-shaped piece of stainless steel was attached to one end of each device using an elastomeric silicone tube to aid in fluoroscopic and radiographic localization of the devices. Also, a continuous loop of suture was passed through the opposite end of each device to act as a tether.

A device was surgically introduced into the external jugular vein in each of four adult Greyhound dogs. The tethering suture was used to affix the device to the wall of the vein. At seven days post-implantation, the devices were retrieved.

One of the devices retrieved from the animals yielded the following viability estimates by three different methods of assessment: 56% by glucose consumption, 62% by Live/Dead™ Viability/Cytotoxicity Assay, and 58% by insulin production. Overall, this particular device showed after seven days in vivo a viable population of cells that was 50–60% the size of its pre-implantation value.

Any viability demonstrated after seven days of in vivo implantation is indicative of proper functioning of the device as defined by transport of nutrients to the cell mass. It has been previously noted that the viable population which can be sustained within a device depends on the concentrations of nutrients in the environment external to the device. This may explain the decrease in viable population observed when the device was removed from tissue culture media and implanted in the animal. Alternatively, this viability estimate may be spuriously low as the device was exposed to adverse conditions during retrieval from the animal. Assessment of viability in the other three devices was compromised by experimental difficulties, and the results are not interpretable in a meaningful fashion.

While we have hereinbefore described a number of embodiments of this invention, it is apparent that the basic constructions can be altered to provide other embodiments which utilize the methods and devices of this invention. Therefore, it will be appreciated that the scope of this invention is defined by the claims appended hereto rather than by the specific embodiments which have been presented hereinbefore by way of example.

We claim:

1. An enclosable cell encapsulating device comprising:

a) an outer porous polytetrafluoroethylene permeable membrane wherein said permeable membrane allows for passage into said device of nutrients external to said device and wastes of cells and desirable cell products out of said device without permitting passage of cells therethrough;

b) a cell displacing flexible polymer core having a plurality of ridges and valleys running lengthwise along said core, situated in said device so as to displace cells from a region centrally located in said device, said core being substantially cell free;

c) a cell zone capable of containing cells, said cell zone having a thickness extending from said permeable membrane to an outer boundary of said cell displacing core, said thickness being sufficiently narrow to support the viability of cells; and d) a sealable opening for receiving cells, which when sealed forms a completely enclosed cell encapsulation device.

* * * * *